(12) United States Patent
Parekh et al.

(10) Patent No.: US 6,902,724 B1
(45) Date of Patent: *Jun. 7, 2005

(54) ENHANCED EFFICACY BASIC ALUMINUM HALIDES, ANTIPERSPIRANT ACTIVE COMPOSITIONS AND METHODS FOR MAKING

(75) Inventors: Jawahar C. Parekh, Livingston, NJ (US); Pradip Amin, Edison, NJ (US)

(73) Assignee: Reheis, Inc., Berkeley Heights, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/807,996

(22) Filed: Mar. 24, 2004

(51) Int. Cl.$^7$ .............................. A61K 7/32; A61K 7/34; A61K 7/38; A61K 7/00
(52) U.S. Cl. ............................ 424/65; 424/66; 424/68; 424/400; 424/401
(58) Field of Search .............................. 424/65, 66, 68, 424/400, 401

(56) References Cited

U.S. PATENT DOCUMENTS

| | | | |
|---|---|---|---|
| 4,359,456 A | 11/1982 | Gosling |
| 4,490,354 A | 12/1984 | Meriwether |
| 4,775,528 A | 10/1988 | Callahan |
| 4,818,512 A | 4/1989 | Markarian |
| 4,859,446 A | 8/1989 | Abrutyn |
| 4,871,525 A | 10/1989 | Giovanniello |
| 4,900,534 A | 2/1990 | Inward |
| 4,944,933 A | 7/1990 | Inward |
| 5,356,609 A | 10/1994 | Giovanniello |
| 5,358,694 A | 10/1994 | Giovanniello |
| 5,595,729 A | 1/1997 | Barr |
| 5,626,827 A | 5/1997 | Barr |
| 5,718,876 A | 2/1998 | Parekh |
| 6,024,945 A | 2/2000 | Parekh |
| 6,042,816 A | 3/2000 | Shen |
| 6,149,897 A | 11/2000 | Swaile |
| 6,436,381 B1 | 8/2002 | Carrillo |
| 6,451,296 B1 | 9/2002 | Li |
| 6,649,153 B1 | 11/2003 | Parekh |

FOREIGN PATENT DOCUMENTS

| | | |
|---|---|---|
| EP | 0586235 B1 | 3/1994 |
| GB | 2048229 A | 12/1980 |

OTHER PUBLICATIONS

Rueller, H.H. and Luedders, W.L., *Pharmacologic and Toxicologic Effects of Topically Applied Agents on the Eccrine Sweat Glands*, Advances in Modern Toxicology, 1977, 4:1–59, Hemisphere Publishing Corp., Washington.

Murphy, Thomas D. and Levine, Mark J., *Analysis of Antiperspirant Efficacy Test Results*, Journal of the Society of Cosmetic Chemists, May–Jun. 1991, 42:167–197.

Quatrale, Richard P., et al., *The Mechanism of Antiperspirant Action by Aluminum Salts: The Effect of Cellophane Tape Stripping on Aluminum Salt–Inhibited Eccrine Sweat Glands*, Journal of the Society of Cosmetic Chemists, Mar.–Apr. 1981, 32:67–73.

Quatrale, Richard P., et al., *The Mechanism of Antiperspirant Action by Aluminum Salts: Histological Observations of Human Eccrine Sweat Glands Inhibited by Aluminum Chlorohydrate*, Journal of the Society of Cosmetic Chemists, May–Jun. 1981, 32:107–136.

Quatrale, Richard P., et al., *The Mechanism of Antiperspirant Action by Aluminum Salts: Histological Observations of Human Eccrine Sweat Glands Inhibited by Aluminum Zirconium Chlorohydrate Glycine Complex*, Journal of the Society of Cosmetic Chemists, Jul.–Aug. 1981, 32:195–221.

Quatrale, Richard P., et al., *The Site of Antiperspirant Action by Aluminum Salts in the Eccrine Sweat Glands of the Axilla*, Journal of the Society of Cosmetic Chemists, Nov.–Dec. 1985, 36:435–440.

*Primary Examiner*—Shelley A. Dodson
(74) *Attorney, Agent, or Firm*—Arthur J. Plantamura (57) ABSTRACT

Disclosed are basic aluminum halides having enhanced antiperspirant efficacy; methods of making such materials and antiperspirant compositions containing such basic aluminum halides, and optionally an amino acid, salts of amino acids, antimicrobial agents, or an organic solvent having at least two carbon atoms and at least one hydroxy group and mixture thereof and methods of making such mixtures. Basic aluminum halides having enhanced antiperspirant efficacy are produced by reacting (a) aluminum powder; (b) an aluminum halide; and (c) water at a temperature greater than about 85° C. This reaction is maintained until reaction products having an Al:halide ratio of about 1.2:1 to 1.5:1 and preferably 1.3 to 1.4:1; and a solution solids concentration of about 30–40 weight percent on an anhydrous basis are obtained. The products are characterized as having a Size Exclusion Chromatography (HPLC) Test Band I of less than 5%, preferably less than 1%, Band II percent aluminum value of 20–60% preferably about 35 to 55%, Band III percent aluminum value of 10 to 35% preferably 15–30% and Band IV value of 15 to 50% and preferably 25 to 35% and sum of peak 3 and 4 areas of at least 45% and no more than 70% and preferably 65%. The enhanced efficacy basic aluminum chloride salts of this invention are more economical to produce, show enhanced efficacy and are more stable compared to the conventional enhanced efficacy aluminum salts which show rapid degradation of Band III to Band II peak areas ratio are less irritant and more skin friendly.

33 Claims, 2 Drawing Sheets

ENHANCED EFFICACY BASIC ALUMINUM HALIDES, ANTIPERSPIRANT ACTIVE COMPOSITIONS AND METHODS FOR MAKING

BACKGROUND OF THE INVENTION

This invention relates to novel antiperspirant compounds comprising basic aluminum halides that have a particular molecular size distribution as well as the processes for their production and their use in antiperspirant composition. Basic aluminum halides, particularly chlorides, and their use as effective antiperspirant compounds are well known. Basic aluminum halides are complex structures made up of mixtures of polymeric and monomeric species of various sizes and molecular structures, depending upon their Al:Halide ratio, together with varying amounts of bound or coordinated water. The basic aluminum compounds are generally represented by the empirical formula:

$$Al_2(OH)_{(6-x)}Y_x \cdot nH_2O$$

wherein Y is Cl, Br or I and 0<x<6 and n is about 0.8 to 4. It should be understood that the above formula is simplified because it is intended to include basic aluminum halides containing coordinated or bound molecules of water as well as basic aluminum halide polymer complexes and mixtures of the above.

Many attempts have been made to improve the antiperspirant efficacy and other properties of basic aluminum compounds, by altering its polymeric structure. The enhanced efficacy salts are typically differentiated from the conventional antiperspirant salts by reference to the various aluminum peaks that can be identified when the salt is analyzed by size exclusion chromatography typically HPLC (high pressure liquid chromatography). A suitable chromatographic technique is capable of resolving the Al in aluminum chlorohydroxide in at least four distinct peaks labeled peaks 2 (which includes peak 1 and peak 2), 3, 4 and 5. The retention time at which these peaks appear, their resolutions and their respective peak areas, are the function of the column (or columns) and mobil phase used. In general, enhanced efficacy salts have been described as having an increased peak 4 content, or an increased peak 4 to peak 3 ratio, compared to conventional (unactivated) salts. In several cases, enhanced efficacy salts have been described as having increased "Band II". It is important to note that generally, Bands I, II, In and IV of one system correspond respectively to peaks 1 and 2 (Band I), 3, 4 and 5 of the other system.

A review of the prior art shows that the known enhanced efficacy salts (measured at 10% solutions) have an HPLC peak 4 to peak 3 area ratio of 0.5 or higher with at least 70% and preferably at least 80% of the aluminum contained in peaks 3 and 4. Thus, enhanced salt will have peak 4 content of at least 20%, and more likely at least 30%, of the total aluminum contained in all the peaks as measured by peak area. In contrast, conventional non-enhanced antiperspirant salt have peak 4 content of the range of about 10% and peak 4 to peak 3 area ratio from about 0.10 to 0.2 or less.

The following is a brief review of the prior art for the preparation of enhanced efficacy aluminum chlorohydroxide powders. Aluminum chlorohydroxides have been reported to be made of three broad basic groups based on their complexing rate with ferron (2-hydroxy-7iodo-5-quinoline sulphonic acid) and have been referred to as $Al^a$, $Al^b$ and $Al^c$. Ala has the fastest complexing rate; the Alb group has an intermediate complexing rate and the $Al^c$ group has the slowest complexing rate. It is also known that when aqueous solutions of aluminum chlorohydoxides are subjected to size exclusion chromatography, the three groups exhibit different retention times. The $Al^a$ group has the longest retention time, which is indicative that it is made up of the lowest molecular size materials, the $Al^b$ group has an intermediate retention time, indicating it comprises complexes of intermediate molecular size and the $Al^c$ group has the shortest retention time indicating that it is made up of the highest molecular size complexes.

U.K. Patent Application GB 2,048,229 A of Fitzgerald reported that there is a further group of complexes within the aluminum chlorohydroxides which has not been previously identified and is more efficacious as an antiperspirant than the known groups referred to above. This more efficacious group was referred to as $Al^c$ and is usually present in amounts from about 10% to 30% by weight in aluminum chlorohydroxide and that aluminum chlorohydroxides can be modified so as to contain substantially higher amount of the $Al^c$ group. The increase in $Al^c$ group is achieved by diluting aluminum chlorohydroxide solution with water to achieve concentration of at least 5% by weight, preferably 7.5% and more preferably 10% by weight or more, and aging the solution at a temperature above 50° C. and below 100° C. until the desired conversion is achieved. Good results were obtained at concentration between 10% and 25% (page 2, line 3 of that reference); these parameters are outside those employed in the process of the present invention.

In U.S. Pat. No. 4,359,456 of Gosling, et al., it is disclosed that basic aluminum halides obtained by conventional method can be further broken down from high molecular weight polymers by diluting concentrated solutions thereof to lower aqueous concentrations (aluminum concentration of 10% to 35% by weight) and heating at a temperature of 50° C. to 140° C. for a period of time sufficient to provide a Band III percent aluminum value of at least 20%. The patent is silent concerning the distribution of, and any significance attributable to, aluminum species in Bands other than Band III. Notable also is the fact that process parameters are different from the present invention.

In U.S. Pat. No. 4,775,528 of Callahan, et al., it is reported that enhanced efficacy Al/Zr product is achieved by heating a 2% to 20% by weight aqueous solution of aluminum chlorohydroxide until the ratio of the height of the peak 4 corresponding to $k_d=0.7$, i.e., Band III, to that of peak corresponding to $k_d=0.5$, i.e., Band II, is at least 2:1 and at least 80%, and preferably at least 90%, of the total aluminum is present within the peaks corresponding to peaks 4 and 3 (Bands III and II) (Column 2, lines 60–61). The resulting product contains lower molecular weight polymers to increase efficacy, but also has a wider polydispersity. The antiperspirant composition comprises zirconyl hydroxy chloride solution and an amino acid to provide an atomic ratio of Al:Zr from 6:1 to 1:1. There is no range or specification delineated for aluminum species in peaks 1 and 2 and peak 5. Peak 4 should have at least 53% of aluminum species to meet the requirements (a) of peak 4 to peak 3 area ratio of at least 2:1 and (b) sum of peaks 4 and 3 areas to be 80% of the total aluminum present within all the peaks.

U.S. Pat. No. 4,818,512 of Markarian discloses a process for preparing enhanced efficacy aluminum chlorohydroxide product containing from about 77% to about 85% of an aluminum chlorohydroxide molecular species having a $k_d$ value of equal to about 0.4 (Band III species) comprising heating an about 5% aqueous solutions of aluminum chlorohydroxide at a temperature of from about 60° C. to about 132° C. and for a period of from about 30 minutes to about three months to produce a reaction product and spray drying the reaction product.

It also reported the effect of the concentration of aluminum chlorohydroxide (a series of 5/6 basic aluminum chlorohyroxides were prepared ranging in concentration from 5% to 25% by weight) solution, the time of heating and the temperature of heating on the distribution of various molecular species of aluminum. For convenient reference the following results are reproduced from Table 1, Column 6 of U.S. Pat. No. 4,818,512.

TABLE I

| | TEMP. | | | % Peak Height | | | |
|---|---|---|---|---|---|---|---|
| CONC. | (° C.) | TIME | pH | $K_d = 0$ | $K_d = 0.25$ | $K_d = 0.4$ | $K_d = 0.6$ |
| 5% | 60* | 3 M | 4.58 | 1 | 18 | 77 | 4 |
| 10% | 60 | 3 M | 4.41 | 1 | 29 | 66 | 4 |
| 15% | 60 | 3 M | 4.33 | 3 | 43 | 52 | 2 |
| 20% | 60 | 3 M | 4.25 | 9 | 48 | 39 | 5 |
| 25% | 60 | 4.8 M | 4.00 | 41 | 39 | 17 | 4 |
| 25% | RT | 0 (initial) | 4.26 | 71 | 18 | 6 | 4 |
| | | | | Band I | Band II | Band III | Band IV |

These results disclosed by U.S. Pat. No. 4,818,512 clearly demonstrate that at higher concentrations (25% or higher) the percent of lower molecular Band III and Band IV species obtained is very low (less than 20% and 5% respectively) despite aging at an elevated temperature for more than 3 months. Such compositions and process parameters of the '512 patent are clearly outside the range of those contemplated by the present invention.

In U.S. Pat. No. 4,859,446 of Abrutyn is disclosed an improved process for preparing an enhanced antiperspirant which is characterized by size exclusion chromatograph corresponding to Band III of the standard Basic Aluminum Chloride solution and a Band III percent aluminum value of at least 40% which comprises reacting an aluminum compound of the formula: $Al_nX_m$, wherein X is Cl, Br, F, I, $SO_4$ and $NO_2$, n is 1 or 2 and m is 1 or 3, with aluminum metal in an aqueous medium at a temperature between 50° C. and 195° C. until a ratio of aluminum to anion of 0.50–2.5:1 is obtained and recovering the resultant product without elevated temperature aging. Here also the product composition is different from the product of this invention as characterized by HPLC and the process is different.

In U.S. Pat. No. 4,871,525 of Giovanniello is disclosed a process which comprises heating in water at a temperature from about 50° C. to about 100° C. aluminum metal preferably in the form of pellets or powder, with a halogen containing compound selected from HXn, where X is chlorine, bromine or iodine. The amount of water used is such as to have concentration of the polymer in percent by weight in the range from about 8% to about 35% preferably from about 15% to about 25% and more preferably from about 17% to about 22% by weight. The reaction temperatures are preferably in the range from about 95° C. to about 100° C. and should not be high enough to create reflux conditions. 100% of the aluminum containing polymers are found in Bands II, III and IV and Band III contains at least 20% of the total aluminum polymers. Narrow polydispersity is claimed when the batch concentration falls within 17–22% and metal to chloride atomic ratio does not exceed 2.00:1. The product of the '525 patent differs from the U.S. Pat. No. 4,359,456 and U.S. Pat. No. 4,775,528 patents in that '525 patent claims zero aluminum species in Band I. However, none of the three patents disclose, teach or suggest compositions containing specific aluminum species concentration in peak 5 or Band IV.

U.S. Pat. No. 4,900,534 of Inward discloses a process for the direct preparation of aluminum zirconium halohydrates of enhanced efficacy having size-exclusion chromatograph of which the Band III proportion is at least 20%. However, the process parameters and product characterization disclosed in that patent differ significantly from those of the present invention.

U.S. Pat. No. 4,944,933 of Inward discloses a process for the manufacture of basic aluminum chloride solutions with 7.5% to 13% by weight, having an aluminum chloride molar ratio in the range of 1.7 to 2.2:1 and which has Band III fraction of at least 20% and drying the final basic aluminum chloride solution to give hydrated powder having Band III fraction of at least 20%. This patent also does not teach the significance of the concentration of aluminum species in Bands II and IV and Al:Cl molar ratio is outside the range of the current invention.

U.S. Pat. Nos. 5,358,694 and 5,356,609 of Giovanniello disclose a process which comprises reacting aluminum metal with hydrohalogen acid having the formula HX wherein X is Cl, Br and I or with aluminum halide hexahydrate $AlX_3.6H_2O$ wherein X is Cl, Br or I, at a temperature of about 50° C. to about 100° C. the concentration of the product being 8% to about 25% by weight of the solution. The basic aluminum compound wherein the Al/halide ratio is about 1:1 to 2.1:1 is recovered from the hot solution by spray drying. 100% of the polymers are found in Bands II, III and IV with no part of the product found in Band I. Band III of the product contains at least 25% of the polymer. Aluminum metal may contain reaction catalyst comprising metal wherein the metal is copper utilized at about 0.005 to about 0.3 weight percent or iron utilized at about 0.02 to about 0.25 weight percent based on the weight of aluminum. Aluminum species concentration range in Bands II and IV is not defined.

U.S. Pat. Nos. 5,595,729, 5,626,827 of Barr, et al., disclose antiperspirant active compositions comprising basic aluminum material having the empirical formula $Al_2(OH)_{6-a}X_a$ where $0.5 \leq a \leq 5$ and X is a univalent complex oxo anion of nitrogen or a univalent complex oxo anion of a halogen (for example, $NO_3$, $ClO_3$, $ClO_4$ and $IO_4$) being further characterized by chromatography peaks corresponding to peak 3 and peak 4 of the size exclusion HPLC chromatogram with a peak 4 (Band III) relative area of at least 25% and peak 3 (Band II) relative area of less than 60%, the sum of the relative peak 3 and peak 4 (Band II and Band III) area being at least 50% and peak 1 less than 10% (chromatographic peaks eluting at shorter retention times than peak 3 corresponding to peaks 1 and 2). The product of that patent is particularly directed to basic aluminum antiperspirant materials containing a univalent complex oxo anion of nitrogen or halogen and not to halogen anion alone and does not require any specific concentration of aluminum species in peak 5 or Band IV.

U.S. Pat. No. 6,149,897 of Swaile discloses a process for making anhydrous compositions containing solubalized enhanced aluminum zirconium antiperspirant wherein the weight ratio of the anhydrous solvent to the zirconium containing and aluminum containing antiperspirant active is from about 1:2 to 20:1 and peak 3 to peak 4 (Band II to Band III) area ratio is at least 0.1:1. The atomic ratio of zirconium to aluminum is from 1:1 to about 4:1. The patent contains no disclosure concerning the concentration of polymeric aluminum species as expressed by the areas of Band I and Band IV. The requisite process parameters and composition of the present invention are outside those employed in the patent.

U.S. Pat. No. 6,451,296 B1 of Li, et al., discloses stable aluminum zirconium antiperspirant compositions in polyhydric alcohol solution with enhanced efficacy having 20–45% by weight concentration on an anhydrous basis and wherein the aluminum to zirconium atomic ratio is from 10:1 to 1:10. The amino acid to zirconium molecular ratio is 0.1 to 2:1 and aluminum and zirconium to anion ratio is from 0.9:1 to 2.1:1. The product is further characterized by Band I relative area value of from 0% to 5% and Band III and IV relative area values of at least 75%.

The patent teaches preparation of stable enhanced efficacy Al/Zr solution by employing polyhydric alcohol as one of the reactants and anti-gelling agent for zirconium. The presence of zirconyl oxychloride promotes depolymerization of aluminum species and yields higher concentration of lower molecular weight species resulting in higher concentration of peak 4. The presence of polyhydric alcohol as an anti-gelling agent minimizes polymerization of zirconium species. However, the high concentration of polyhydric alcohol is not desirable for most antiperspirant formulations due to its tackiness. The novel product of this invention is prepared in the absence of polyhydric alcohol and/or zirconyl chloride.

The process parameters used for the activation of basic aluminum chloride by an indirect process (i.e., heating and or aging a diluted solution) or by direct process where aluminum metal in powder or pellet or other forms is reacted with HX or $AlX_3.6H_2O$, wherein X is Cl, Br or I, are clearly outside those employed by the process of the present invention and no prior art has defined composition of basic aluminum halides in terms of concentration of aluminum species in all the four bands to achieve superior efficacy while minimizing the irritancy potential, acid odor associated with low metals to chloride (0.9:1 to 1:1) and making it economically.

The prior art emphasizes and attributes higher efficacy primarily to the increase in concentration of Band III or peak 4 species. The Parekh, et al., U.S. Pat. No. 5,718,876 demonstrates that Band II percent aluminum value of at least 50% and Band III percent value of less than 20% also give enhanced efficacy antiperspirant products. The Carrillo, et al., U.S. Pat. No. 6,436,381 correlated improved efficacy of low metal to chloride ratio (0.9:1 to 1:1) products with peak 5 (or Band IV). Carrillo et al., pointed out that basic aluminum chloride with significant amount of peak 5 (Band IV) is not known to have any efficacy advantage and is not typically used in commercial products thus that disclosure teaches away from the basic aluminum halide with significant amount of peak 5. The invention of U.S. Pat. No. 6,436,381 does not embrace the aluminum antiperspirant salts and is directed only to aluminum-zirconium salts having a substantial peak 5. No other prior art known has demonstrated that significant improvement in efficacy can be obtained by controlling concentration of species present in Bands I, II, III and IV while maintaining Al:Cl ratio in the range of 1.2:1 to 1.5:1 and preferably 1.3:1 to 1.4:1 and at high anhydrous solids (30–40%) concentrations. This is achieved by careful control of the metals to chloride ratio, maintenance of proper solids concentration and with or without aging at room temperature.

Basic aluminum chlorides having a preponderance of Band III aluminum species and process for the production of such compounds have a number of disadvantages; for example, these processes generally require either dilution of conventional aluminum chlorohydroxide to 5–20% weight concentration or thermal treatment of dilute solutions at high temperatures to effect the polymer conversion and then rapid drying of the solution into a powder form as the solution itself is not stable. Alternately, the solution can be prepared directly by reacting aluminum powder or pellets with HX or $AlX_3.6H_2O$ in an aqueous phase at a lower weight percent concentration, for example, 15–20%. In any case, the cost of drying the dilute solution to powders is significantly higher. All of the cited prior art, except one, attributes higher efficacy to increase concentration of Band III (peak 4) aluminum species; the concentration ranging from at least 20% to as high as 85%.

U.S. Pat. Nos. 5,718,876 and 6,024,945 of Parekh, et al., disclose preparation of enhanced efficacy basic aluminum halides solutions having solids concentration of about 28% to about 42% on an anhydrous basis having Al:anion ratio of about 1.2 to 1.8 and having Band II percent aluminum value of at least about 50% and Band III percent aluminum values of less than 20% and Band I percent aluminum value of less than about 1%. The basic aluminum chlorides of the process disclosed herein overcame the disadvantages of the prior art and demonstrated excellent antiperspirancy. The disclosure of U.S. Pat. Nos. 5,718,876 and 6,024,945 are incorporated herein by reference.

It is important to note that the weight percentage of antiperspirant salt is indicated herein as percent of anhydrous solid (% A.S.), which excludes any bound water. This is calculated in accordance with the following equation:

$$\% A.S. = \% Al[26.98x+17.01(3x-1)+35.453]/26.98x$$

wherein x=Al/Cl ratio.

The following comparison illustrates the difference in the calculation of antiperspirant salt between the present method and the previous standard industry method.

TABLE II

| Salt | Standard Method | Present Method |
|---|---|---|
| 5/6 Basic aluminum chlorohydrate solution | 50% w/w | 40.8% |

Thus, 28% anhydrous solids refers to 34.3% weight percent solution using the standard method.

In the above mentioned U.S. Pat. No. 5,718,876 basic aluminum halides and nitrates are prepared by reacting an aluminum powder, an aluminum halide or nitrate solution and water at a temperature greater than about 85° C. The reaction is maintained until reaction products having an Al:anion ratio of about 1.2 to about 1.8 and a solution solids concentration of about 28 to about 42 weight percent on an anhydrous basis are obtained. The reaction product is characterized as having a Size Exclusion Chromatography Test Band having a Band II percent aluminum value of at least about 50% and Band III percent aluminum value of less than 20%. Those products preferably also have a Band I percent aluminum value of less than about 1%. The method of that patent also encompasses the preparation of basic aluminum halide, nitrate and zirconium complexes. The zirconium compounds are preferably buffered with amino acid. The method of that patent for preparing these compounds comprises reacting, at room temperature, a basic aluminum halide and nitrate solution, with a zirconium compound or a zirconium/amino acid complex. The products obtained have a preponderance of aluminum species in Band II and the basic aluminum halide and zirconium complexes of these compounds provide improved efficacy when made into an antiperspirant composition using any of the usual vehicles of formulations known in the art.

SUMMARY OF THE INVENTION

Whereas, the products obtainable according to U.S. Pat. No. 5,718,876 are characterized as having a metals to chloride ratio between 1.2 to 1.8, a solution solids content of about 28% to about 42% anhydrous solids by weight percent, and have a size Exclusion Chromatography Test Band with a relative retention time corresponding to Band II of a Standard Basic Aluminum Chloride Size Exclusion Chromatogram, and a Band I percent aluminum value of less than 1%, a Band II percent value of greater than 50% and a Band III percent value of less than 20%, as distinguished therefrom, those of the present invention are characterized as having a metal to chloride ratio of between 1.2 to about 1.5 (vs. 1.2–1.8) preferably between 1.3 to 1.4 and a solution solids content maintained within a relatively narrow range of about 30% to about 40% (vs. 28–42%) anhydrous weight percent and Size Exclusion Chromatography Test Band with a Band I percent aluminum value of less than 5% (vs. less than 1%) a Band II value about 20–60% (vs. greater than 50%) a Band III value between about 10% and 35% (vs. less than 20%) and a Band IV value between 15 to 50% (vs. no mention of Band IV).

Accordingly, it is an object of the present invention to provide a novel enhanced efficacy basic aluminum halide antiperspirant actives which can be produced economically.

It is another object of the present invention to provide such basic aluminum halide antiperspirants with substantially enhanced relative efficacy and to provide methods of forming such materials without the need for manufacturing steps previously thought to be necessary of heating diluted solutions of already manufactured basic aluminum halides at high temperatures and/or pressure conditions.

It is another object of the present invention to provide methods of forming enhanced efficacy basic aluminum halide solutions that have high concentrations thereby minimizing spray drying cost.

It is yet another object of the present invention to provide antiperspirant compositions having enhanced antiperspirancy and skin friendliness.

It is another object of this invention to provide a process for the preparation of an activated aluminum halide composition, which has improved stability and does not require rapid drying after the desired solution is made which is a limitation applicable to most of the prior art enhanced efficacy products.

In accordance with the discovery of the present invention, a careful control of the metals to chloride ratio, maintenance of a suitably proper solution solids concentration and aging of the solution at room temperature, yields a product characterized as having a significantly more desirable size exclusion chromatography test band profile and superior efficacy.

DETAILED DESCRIPTION OF THE INVENTION

The term "enhanced efficacy antiperspirant active" is used interchangeably herein with the terms "activated antiperspirant active" or "improved efficacy antiperspirant" active. The enhanced antiperspirant contemplated herein means any aluminum containing antiperspirant material whose polymeric form is measurably shifted to lower molecular weight polymers relative to the polymer distribution of a typical aluminum chlorohydroxide (5/6 basic aluminum chloride). The measurable shift is determined by high-pressure liquid chromatography as described herein. In the analyses each sample is dissolved in deionized water to form about 5 mg/ml aluminum solution and filtered through a 0.45% filter and chromatographed within 5 minutes using 10 microliter samples at a flow rate of 0.7 ml/min at a pressure of 450–500 psig and 0.01N HNO3 eluent. Two chromatographic columns used in series are a Waters Porasil column 30 cm long with an ID of 3.9 mm, a pore size of 125° A, particle size of 10$\mu$ and a Phenomenex Column 25 cm long with an ID of 4.6 mm, a pore size of 60° A and particle size of 10$\mu$. A Waters 2414 Differential Refractometer was used to scan chromatograph. Relative peak areas, and peak heights were calculated using Waters Millenium[32] Chromatography Manager.

Figure 1:
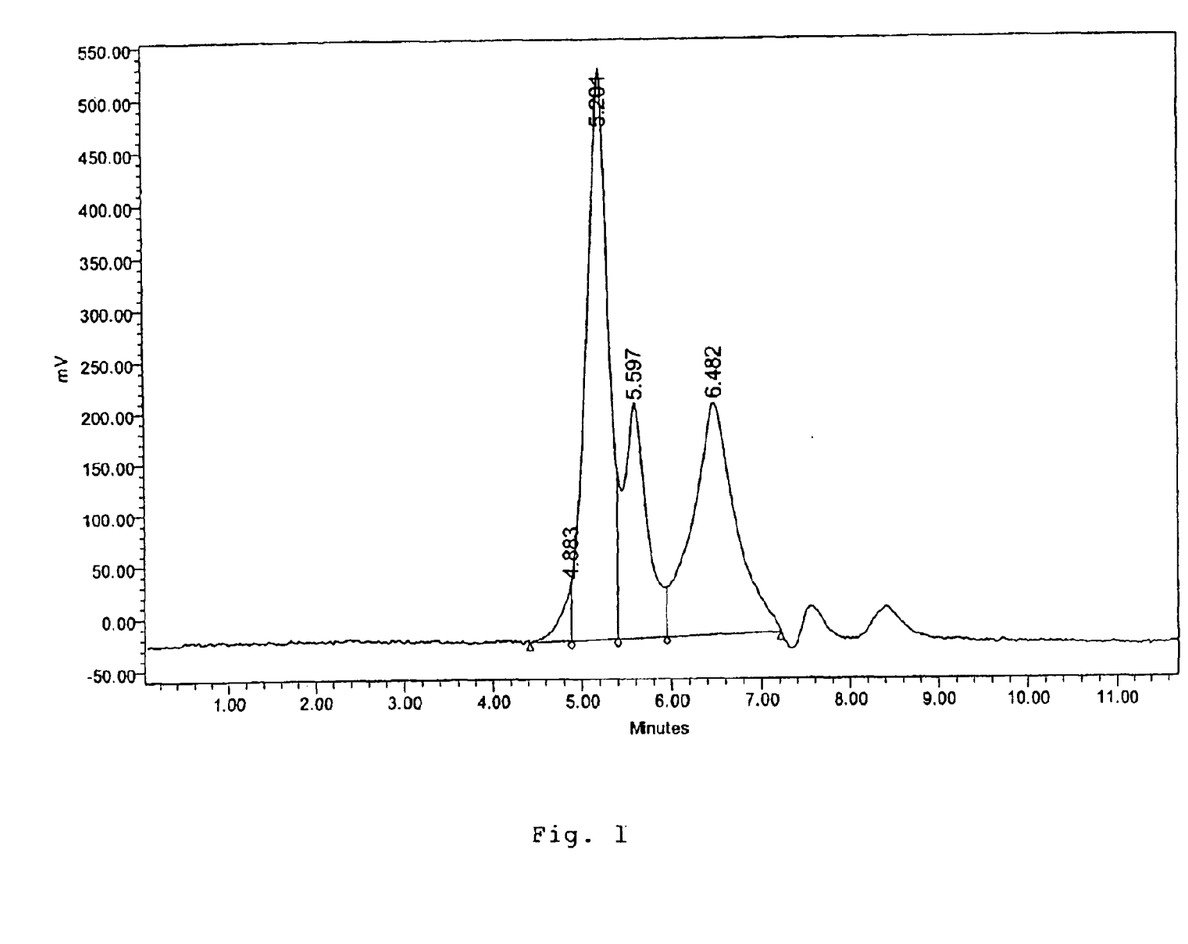
FIG. 1 is a typical chromatograph of basic aluminum chloride powder.

The peaks observed in the chromatogram are designated in order of appearance on the chromatograms as peaks 1–2, (appears as a single peak, Band I) and peak 3 (Band II), peak 4 (Band III) and peak 5 (Band IV). (See FIG. 1) The area of the peaks correspond to the relative concentration of aluminum polymer species exiting the column during the specified time passed from the injected sample.

The term "metal/chloride ratio" is used interchangeably herein with Al:Cl ratio or metal/anion ratio and the ratio always refers to atomic ratio.

The basic aluminum halides prepared in accordance with the present method are characterized as having metal to chloride ratio between 1.2:1 to about 1.5:1, preferably between 1.3:1 to 1.4:1 and solution solids content maintained within a relatively narrow range of about 30 to 40 anhydrous weight percent and having Size Exclusion Chromatography Test Band with Band I percent aluminum value of less than 5%, preferably less than 1%, Band II percent aluminum value of 20 to 60%, preferably about 35 to 55%, Band III percent aluminum value of 10 to 35%, preferably 15 to 30% and Band IV value of 15 to 50%, preferably 25 to 35% and peaks 3 and 4 area is at least 45% and not greater than 70% preferably not greater than 65%. There is no limitation on peak area ratio Band III/II; it can be significantly less than 0.4, as in Examples 1, 5, 6 and 8.

The present method comprises reacting (a) aluminum powder (b) an aluminum halide solution and (c) water. Examples of the aluminum powder are such as Ampal grade 601, Alcoa grade 101 and Alcan grade 52R.

In general, any standard aluminum halide conventionally used in the art may be used in the present method. Such solutions generally have a solution solids concentration of about 28 weight percent. This corresponds to an aluminum content of about 5.7%. However, it will be evident to one skilled in the art that aluminum halide solutions having other concentrations may also be used in the present method.

The three components employed in the method of the present invention, i.e., the aluminum powder, the aluminum halide and water, should be reacted at a temperature greater than about 85° C. Preferably, the components are reacted at a temperature of about 91° C. to about 95° C.

The reaction is maintained until a desired reaction product having an Al:halide ratio of about 1.2 to about 1.5 and a solution solids concentration of about 30 to about 40 anhydrous weight percent is obtained. When the desired reaction product is obtained, the reaction product is cooled, filtered and aged at room temperature until the desired HPLC is obtained. The product is then dried by any appropriate means known to those skilled in the art, preferably by spray drying to a powder form. Such products have a pH of 15% w/w solution of at least 3.5 and are characterized by having a reduced probability of irritancy to the skin compared to products having Al:Cl ratio of 0.9:1 to 1:1. The Al:halide ratio, solution solids concentration and solution aging have been found to be critical in obtaining antiperspirant products of superior efficacy economically.

The basic aluminum halides of the present invention may also be prepared by an "indirect process" which comprises taking a conventional basic aluminum halide solution having a suitable Al:halide ratio that is adjusted to an Al:halide ratio of the solution to about 1.2:1 to 1.5:1, preferably 1.3:1 to 1.4:1, by adding an appropriate either aged or unaged lower basicity aluminum halide solution or HX or $AlX_3.6H_2O$, where X can be Cl, Br or I solutions thereto. This adjusted composition may be heated to 95–100° C. for a period that may range from about 10 minutes to about 6 hours and may be aged at room temperature until the desired chromatographic distribution of aluminum species is obtained, i.e., until the products of this process comprise the desired Band I, II, III, and IV percentages.

The products derived by the present invention reduces irritancy potential by employing higher Al:Cl ratio 1.3 to 1 while delivering enhanced efficacy. The irritancy potential can be further reduced by buffering basic aluminum halides with amino acids or compounds of amino acids. In addition to amino acids per se, such as glycine, amino acid compounds that are useful herein include alkali metal and alkaline earth metal salt of amino acids as well as ammonium or hydroxy salts of amino acids.

As used herein, the term "alkaline" as applied to salts of amino acids, is not intended to be limited to those having a pH greater than 7.0, since some complex or imperfectly neutralized salts can have a pH less than 7.0 and still be useful in this invention. Instead, alkaline is meant to refer to the usual alkali and alkaline earth metal cations, including ammonium and hydroxy cations.

Metal glycinates such as sodium or zinc glycinate or strontium glycinate or mixtures thereof can also be used. Among the salts of amino acids useful herein are those derived from amino acids in which the number of amino groups is equal to the number of carboxyl groups in the molecule. Examples of such amino acids include glycine, DL-valine, alanine, lysine, arginine, and L(−) prolinates. Suitable salts of other amino acids that may be used in the present invention will be evident to those skilled in the art.

Suitable hydroxy salts of amino acids useful herein include the monohydroxy and dihydroxy aluminum salts of amino acids, and aluminum-magnesium-hydroxy-glycine compounds, such as monohydroxy aluminum glycinate, magnesium glycinate and calcium glycinate. These hydroxy salts are the reaction products of aluminum hydroxy antacids and the desired amino salt. Since these glycinates are available in different basicities, the amount of glycinate or other salt to be used depends upon the particular basicity of the amino salt. In general, about 0.5% to 10% by weight of the above salts can be used with the products of this invention. The desirable method is to add the amino acid or the salt of an amino acid or a combination thereof to the basic aluminum halide solution having the desired chromatographic distribution and spray drying the buffered solution.

Other compounds that may be usefully employed in reducing acidity and irritancy potential are disclosed in U.S. Pat. No. 6,024,945 of Parekh which is incorporated here in its entirety by reference.

It is desirable for an antiperspirant product to provide aesthetics (pleasing skin feel) in addition to excellent antiperspirancy. It is also desirable that the basic aluminum halides of this invention have an improved solubility for certain formulation without sacrificing antiperspirant efficacy. This can be achieved by adding a suitable organic solvent such as propylene glycol or polyethylene glycol to the desired basic aluminum halide of this invention and the solution may be heated at about 85–95° C. for about one hour and spray dried. The resultant powder has increased solubility in organic solvents. Also, if the modifying component is a polyhydric alcohol, preferably glycerin, it provides excellent skin conditioning and moisturizing without adversely affecting efficacy of the antiperspirants. Other compounds which can provide skin friendly antiperspirants without sacrificing efficacy are listed in U.S. Pat. No. 6,649,153 B1 the disclosure of which is incorporated here by reference.

The invention is further described by reference to the following illustrate examples, details of which, except as recited in the appended claims, are not to be construed as limitations.

The process used for the preparation of basic aluminum halides of the invention comprises: reacting aluminum powder, an aluminum halide solution and water at a temperature greater than 85° C.; maintaining this reaction until the reaction product having an Al:halide ratio of 1.2:1 to 1.5:1 and a solution solids concentration of about 30% to 42% on an anhydrous basis is obtained; filtering the reaction product; and aging the reaction product at room temperature until the desired chromatographic distribution is achieved.

EXAMPLE 1

1250 gms of 32°Be aluminum chloride solution (chemical analysis % Al=5.55, % Cl=22.19) was diluted with 1050 gms of water in a 4 liter pyrex beaker and heated to 85° C. using a hot plate. The solution was stirred with an overhead mechanical agitator; 206 gms of Alcoa (grade 101) aluminum powder was added slowly with agitation and temperature was controlled at about 95° C.±2° C. and over constant volume. The reaction was complete in 2.5 hours and the basic aluminum chloride (BAC) solution was filtered to yield a clear solution with Al:Cl atomic ratio of 1.315:1. Chemical analysis of the filtered solution was % Al 11.0 and % Cl 11.0. HPLC of the solutions were run initially and at different time intervals after aging at room temperature to study the effect of changes taking place at macromolecular level and to obtain the desired chromatographic distribution of aluminum species. Results are shown in Table III.

TABLE III

| Example Days Aged at R.T. | #1 Al:Cl Molar Ratio 1.315:1 | | | |
|---|---|---|---|---|
| | Band I | Band II | Band III | Band IV |
| 0 | 1.07 | 53.97 | 8.97 | 36 |
| 4 | 0.91 | 50 | 9.68 | 39.41 |
| 13 | 0.37 | 43.56 | 12.48 | 43.6 |

Results of Table III clearly demonstrate that the freshly prepared basic aluminum chloride solutions are not equilibrated and molecular rearrangement takes place on aging at room temperature which can be monitored using chromatographic technique. Gradual depolymerization takes place as Band II species decrease and Band III and IV increase. This process slows down as Al:Cl ratio increases. Thus, it is possible to obtain basic aluminum halide salts with desired aluminum species distribution by monitoring and controlling aging process at room temperature.

EXAMPLES 2–6

Six large scale batches of BAC were prepared at Al:Cl ratio of 1.32±0.02:1 using essentially the procedure of Example 1 and were stored at room temperature and in most cases HPLCs were run after 2 to 9 months of storage at room temperature. Results are shown by Table IV and show that higher Band III concentration are obtained when solutions are aged at room temperature from about 2 to 8 months. Solution stability remains good between 2–8 months based on chromatographic results shown in Table IV. Thus, it is not required, as previously thought as necessary, to rapidly dry the solution within 0.5 hours to 24 hours to preserve the higher efficacy. In contrast, the prior art regarded it as necessary to rapid dry where activated salts are prepared by diluting previously prepared 5/6 basic ACH solution and to subject the product to thermal treatment at high temperatures. Such products show rapid degradation of Band III to Band II peak areas ration and are not economical to produce.

TABLE IV

| Examples | Days aged at R.T. | Al:Cl atomic ratio | HPLC Peak Areas | | | | Band III & IV | % Anhydrous Solids |
|---|---|---|---|---|---|---|---|---|
| | | | Band I | Band II | Band III | Band IV | | |
| 2 | 63 | 1.34:1 | 0 | 40.05 | 24.73 | 35.21 | 59.94 | 39.76 |
| 3 | 71 | 1.34:1 | 0 | 43.33 | 23.71 | 32.96 | 56.67 | 38.79 |
| 4 | 260 | 1.30:1 | 0 | 36.14 | 23.35 | 40.51 | 63.86 | 39.28 |
| 5 | 265 | 1.32:1 | 0 | 40.92 | 14.19 | 44.89 | 59.08 | 38.50 |
| 6 | 2 | 1.34:1 | 0 | 50.12 | 12.63 | 37.25 | 49.88 | 38.10 |

Al:Cl ratio of Example 6 was adjusted to 1.30:1 and was aged for about 93 days at room temperature before spray drying at an inlet temperature of 600° F.–700° F. and an outlet temperature 270° F.–275° F. Chemical analysis and HPLC results where as follows: % Al 25.42, % Cl 22.89, Al:Cl ratio 1.46:1, Band I 3.8%, Band II 42.8%, Band III 29%, Band IV 24.4%.

EXAMPLE 7

45 lbs. of basic aluminum chloride solution having Al:Cl molar ratio of 1.31:1 (% Al 11.5%, % Cl 11.4% and anhydrous solids content 39.18%) prepared using the scaled-up process of this invention and aged for about four and half months at room temperature was blended with 3 lbs. of basic aluminum chloride solution having Al:Cl ratio of 1.69:1 to increase Al:Cl ratio to about 1.4:1 to reduce irritancy potential of the product. The resultant solution was spray dried in a co-current conical bottom spray dryer at an inlet temperature of 550° C. and an outlet temperature of 235° C. to yield powder. Chemical analysis of the powder was % Al 23.2, % Cl 21.4, Al:Cl molar ratio 1.43:1, iron 60 ppm and pH at 15% w/w solution was 3.95, percent anhydrous solids content of the powder was 78.2%. HPLC of the powder showed peak areas for Band I, II, III and IV to be 0%, 45.4%, 18.5% and 35.07% respectively. This product showed superior antiperspirancy when tested using typical clinical study used for evaluation of antiperspirancy.

EXAMPLE 8

Freshly prepared large scale batches of BAC solution having Al:Cl ratio of 1.42:1 (% Al 11.2, % Cl 10.34) was mixed with 32° Be $AlCl_3$ solution to lower Al:Cl ratio to 1.30:1 and the solution was spray dried at an inlet temperature of 465° F. and an outlet temperature of 190° F. after about 24 hrs. of aging at room temperature. Chemical analysis of the powder was: % Al 23.1%, % Cl 21.8%, Al:Cl ratio of 1.39:1 HPLC peak area distributions for Band I, II, III and IV were 1.6%, 50.8%, 13.7% and 33.9% respectively giving Band III/II peak area ratio of 0.27.

The product of this invention obtained in accordance with Example 8 was further characterized by $^{27}Al$ NMR spectroscopy which is the method selected to identify the structures of different aluminum species in the enhanced efficacy aluminum salt. The antiperspirant salt is generally dissolved in deuteriated water ($D_2O$) to form a 10% by weight solution just before the measurement. Data was collected using Varian Inova 400 instrument at 104.2 MHz. (The analysis was done by Spectral Data Services, Inc., Champaign, Ill.). Generally, a sharp peak at chemical shift of 0 ppm indicates the presence of octahedral aluminum monomer species and a sharp peak at 63 ppm indicates the presence of $Al_{13}$ species and a broad chemical shift of 72 ppm is an indication of the presence of tetrahedral $Al_{41}$ species and possibly higher molecular weight species. It is important that the product have maximum depolymerized aluminum species concentration for improved efficacy. $^{27}Al$ NMR analysis of the sample showed a significant increase in depolymerized aluminum species concentration measured as percent of the total area under the spectrum from +100 ppm to −100 ppm that is contained in sum of the areas of resonance lines at or below 10 ppm. For the sample of Example 8 this area totaled to be 71.36%.

In Vitro Test

The novel product of this invention was also subjected to an in vitro test method to investigate its efficacy relative to the known enhanced and non-enhanced efficacy products.

The apparatus and test protocol are based on method described by Reller and Leudders (Reller, H. H. and Leudders, W. L., Advances in Modern Toxicology, 4: 1–59 (1977)) and EP 0586235 B1 disclosures of which are incorporated herein by reference. Reller and Leudders described a millipore system which they used to measure the obstruction caused by the neutralization of various metal salts. They then compared their in vitro findings with those obtained for antiperspirant efficacy of the salts which had been tested in humans and found a reasonable correlation. A modified version of the apparatus and protocol described in EP 058623 B1 were developed and used to determine the relative in vitro efficacy of antiperspirant actives. The system is shown schematically in FIG. 2 of the accompanying drawings. The system consists of four major components, namely the pressure control unit I, the sweat reservoir II, the cell III and the measuring system IV.

Figure 2:
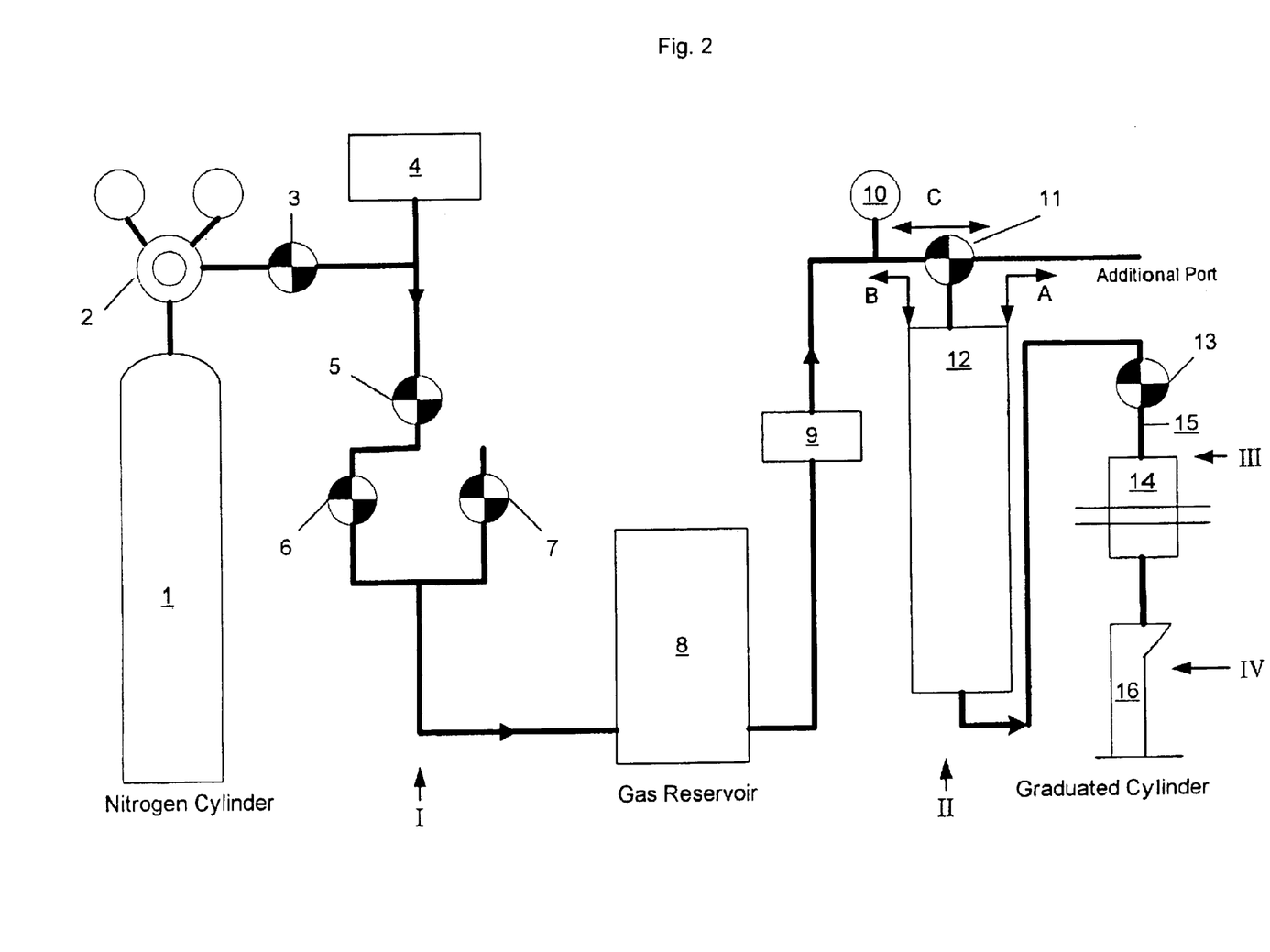
FIG. 2 is a schematic representation of an in vitro apparatus used to determine the relative efficacy of antiperspirant actives.

The pressure control unit I consisted of a standard nitrogen gas cylinder 1 equipped with a pressure regulator 2 and connected to an on/off isolation valve 3 and pressure relief safety valve 4. The on/off valve 3 isolates the nitrogen cylinder 1 from the rest of the system. The majority of connections were made using ¼" stainless steel tubing and swage lock fittings. The primary pressure source from cylinder 1 is followed by a parallel arrangement of needle valve 6, an on/off valve 7, nitrogen gas reservoir 8 and 0.5 micron sintered metal filter 9 to remove any foreign particles. A magnahelic gauge 10 monitors pressure fluctuation within 1" of water over an ambient pressure. The objective is to minimize any pressure fluctuation during the experiment and under ideal conditions the pressure should be substantially constant. The pressure unit system I is capable of maintaining constant pressure of the sweat reservoir II within a reasonable range. It is understood the system is somewhat operator sensitive.

The sweat reservoir II is a plexiglass cylinder 12 having about one gallon capacity. The top end of the plexiglass cylinder 12 is connected to the pressure control system I through a three-way valve 11. The saline solution is fed to the sweat reservoir II with the valve 11 in position "A" and is connected to the reservoir II and to the pressure system I in position "B" and allows the pressure control system I to be purged in position "C".

The bottom end of the reservoir II is hooked up to a filter cell (the "cell") 14 through a rapid action on/off valve 13 by tygon tubing 15. A 5 micron Millipore filter is held in the filter of cell 14 which is made of a suitable plastic that avoids any corrosion and foreign particle contamination.

Discharge from filter cell 14 is collected in a measuring system IV comprising a graduated pyrex measuring cylinder 16 for the flow studies over the predetermined fixed time interval. The system was operated at a pressure of about 100 mm $H_2O$ over the ambient pressure.

The Test Procedure

The procedure comprised of preparing filtered (0.45 micron) DI water, filtered 0.25% NaCl solution and 0.185 molar aluminum solution of basic aluminum halide in filtered DI water. A portion of antiperspirant solution is transferred to a 7.5 cm watch glass and using filter membrane forceps a 5 micron Millipore filter paper is placed into the solution making sure that all the pores of the Millipore filter are wetted. The filter paper is soaked for a total of 180 seconds and then transferred onto bed of the cell 14 which is free of any residual water. Cell 14 bed with membrane is placed into threaded portion of the cell 14 and viton "o" ring is inserted down to the level of the filter membrane. pH 10 buffer solution ($NH_4OH/NH_4Cl$) is then added via a wash bottle slowly in the direction of the cell 14 threads and cell 14 is flooded with the buffer solution. The filter paper is kept flooded with the buffer solution for 300 seconds. After filling cell 14 with a 0.25% NaCl solution, and making sure no air bubbles are trapped, cell 14 is attached to the apparatus. Air is purged from the system and the sweat reservoir II is filled with 0.25% NaCl solution to a predetermined mark. Pressure is adjusted in the system to 100 mm $H_2O$ above the ambient pressure and on/off valve 13 is opened for exactly 10 seconds and during this time needle valve 6 is used to maintain constant pressure. Volume of the liquid collected in the measuring cylinder 16 is recorded. The procedure is repeated three times and the average of the three readings is taken as "blocked" volume. The procedure is repeated three times with 0.25% NaCl solution and average of the three readings gives unblocked flow under the identical condition.

Since fractional filter flow rate reduction is due to blockage of filter paper by the precipitation of aluminum salt in the pores of the filter it is an indirect measure of potential antiperspirancy that the salt may exhibit and was designated as "IVMI" for "In Vitro Model Index" and is computed as follows:

$$IVMI = 1 - \frac{\text{blocked filter flow}}{\text{Unblocked filter flow}}$$

To validate the in vitro model, antiperspirants, which were tested in a standard hot room assessment procedure (which is known to those skilled in the art), were tested and results were used to develop a correlation between "IVMI" and "% Sweat Reduction". Thus, if there is a good correlation, the method is useful to screen prospective antiperspirant products and predict or estimate product efficacy.

Basically, in the standard hot room procedure, human volunteers are subjected to thermal stress and gravimetric determination of the perspiration produced under the thermal stress with and without antiperspirant product applications are made. The data is subjected to analysis of covariance method described by Murphy and Levine (T. D. Murphy and Cosmetic Chemists 42 (May 1991) 167–197) and compared for their percent sweat reduction capacity. Activated aluminum chlorohydrates and unactivated ACH products available under the REACH® brand from Reheis, Inc. of Berkeley Heights, N.J., were tested extensively under controlled hot room conditions. All antiperspirancy tests were conducted by outside independent labs employing "Controlled Hot Room Gravimetric Test" in conformance with FDA guidelines. Results showed that in order of increasing efficacy products are:

Microdry ACH<Reach 501<Reach 301<Reach 101

Microdry ACH—5/6 Basic Aluminum Chloride or Chlorhydrol

Reach 501—Enhanced Efficacy Version of ACH

Reach 301—Enhanced Efficacy Basic Aluminum Chloride with Al:Cl Ratio of about 1.2 to 1.8.

Reach 101—Enhanced Efficacy 5/6 Basic Aluminum Chloride

Samples of (ACH, Reach 501, Reach 301 and Reach 101) were tested for their pore blocking capability using the apparatus and test methods described herein. Results indicated a good inverse correlation (correlation coefficient greater than 0.9) between average values of "% Sweat Reduction" measured by gravimetric method and "IVMI". It must be noted that this relationship is only for enhanced or unenhanced basic aluminum chlorides and may not hold good for other metal salts due to the differences in their precipitation rate, precipitation pH and the nature and type of the precipitate.

The inverse relationship between "IVMI" and "Axillary Efficacy" as measured by gravimetric method is believed to have been caused by a number of factors; the primary factor being the differences in the aluminum species present in each product tested. For example, ACH is highly polymerized and 5/6 neutralized and small amount of additional base causes immediate gelatinous precipitation and blocks the filter. On the other hand, the aluminum chloride which is monomeric and more acidic, the rate of neutralization and the type of precipitate may be different, and particle size distribution of the primary particles may be significantly smaller. It is also known that enhanced efficacy ACH products are more depolymerized and more acidic than ACH and therefore would precipitate differently.

To further confirm this methodology, basic aluminum chloride samples with different basicity and having aluminum to chloride molar ratio of 0.4:1, 0.5:1, 0.68:1, and 1.04:1 were prepared in the lab and tested along with aluminum chloride solution and aluminum chlorohydrate samples. It reconfirmed the inverse linear relationship, thus, ACH solution had high "IVMI" value and aluminum chloride solution had lowest "IVMI" value while it has the highest antiperspirancy among the various aluminum salts (U.S. Pat. No. 4,490,354) which are known to be antiperspirants.

After validating the in vitro model and confirming the inverse linear relationship between "% Sweat Reduction" as measured by gravimetric method and "IVMI"; the product of the present invention (Example 6) was tested using the in vitro model and the predicted "Percent Sweat Reduction" was compared with predicted and actual percentage sweat reduction and results indicated that the product of this invention possesses efficacy at least as good or better than higher Band III (peak 4) enhanced efficacy salt which reverts to non-enhanced form in aqueous solution on storage.

Based on the "IVMI" value of the product of this invention it can be concluded that the product of the invention possesses superior antiperspirancy while reducing irritancy potential and damage to fabric and is more economical to produce. Since the metal salts are more acidic than the skin surface, sweat or plasma, it is inevitable that neutralization will occur to a varying degree depending on the depth of penetration into the skin or down the sweat duct. Ductal diffusion is a function of molecular weight and charge. Thus, lower molecular weight aluminum species of this invention are more likely to give plug deeper down the eccrine gland as has been demonstrated by Quatrale, et al., (The Mechanism of Antiperspirant Action by Aluminum Salts) and in the reference on the effect of cellophane tape stripping on aluminum salt inhibited eccrine sweat glands. (Journal of the Society of Cosmetic Chemists, 32: 67–73 1981; 32: 107–136, 32: 195–122 and 36: 435–440). The relevant disclosures of these articles are incorporated by reference.

It will be apparent from the foregoing that various equivalents and substitutions may be applied by those skilled in the art, such are contemplated as being within the scope of the invention, except to the extent that such may be specifically excluded, by the express language of the appended claims.

What is claimed is:
1. An aqueous antiperspirant active solution comprising:
   (i) basic aluminum halide having the empirical formula

$$Al_2(OH)_{6-x1}Y_{x1}Rp(AA)_q$$

wherein Y is Cl, Br, or 1 and $1.3 \leq x_1 \leq 1.7$, wherein R is an organic solvent having at least two carbon atoms and at least one hydroxy group and p has a value of $0 \leq p \leq 1.0$ and wherein (AA) is amino acid or amino acid compound and $0 \leq q \leq 0.5$ and
   (ii) size exclusion high performance liquid chromatography test band having a Band I relative area value of less than 5%, a Band II relative area value of 20% to 60%, Band III relative area value of 10% to 35% and Band IV relative area value of 15% to 50% and the sum of Band III and Band IV relative area value of at least 45% and no more than 70% and
   (iii) $^{27}Al$ NMR spectrum wherein at least 45% of the total area under the spectrum from +100 ppm to −100 ppm is contained in the sum of the areas of resonance lines at or below 10 ppm and
   (iv) in which the area of the resonance at 63 ppm is less than 0.1% of the total area under the spectrum from +100 ppm to −100 ppm and
   (v) which comprises 30 to 42% by weight of anhydrous basic aluminum halide antiperspirant active in water.

2. The antiperspirant solution of claim 1 formed by mixing with it in aqueous solution natural or synthetic antimicrobial compounds, such as triclosan, triclocarbon, zinc compounds, green tea extract, or neemoil and mixtures thereof.

3. The antiperspirant solution of claim 1 where Y is chloride and Al:Cl molar ratio is 1.3:1 to 1.4 to 1.

4. The antiperspirant solution of claim 1 where Y is chloride and Al:Cl molar ratio is 1.2:1 to 1.5:1.

5. The antiperspirant solution of claim 1 wherein the substituant AA is selected from the group consisting of glycine, DL-valine, alanine, lysine, arginine, and salts of amino acids.

6. The antiperspirant solution of claim 1 where amino acid is glycine.

7. The antiperspirant solution of claim 1 where amino acid compound is an alkali metal, an alkaline earth metal, ammonium or hydroxy salt of an amino acid, a metal glycinate and a hydroxy aluminum salt of an amino acid.

8. The antiperspirant solution of claim 1 where amino acid salt is selected from sodium glycinate, magnesium glycinate, potassium glycinate, calcium glycinate, zinc glycinate and strontium glycinate or mixtures thereof.

9. The antiperspirant solution of claim 1 where an organic solvent is a polyhydric alcohol having at least three to about 12 carbon atoms and at least two hydroxy groups and at a concentration of about 1 to 10 weight percent.

10. The antiperspirant solution of claim 1 wherein organic solvent is polyhydric alcohol and is selected from glycerin, diglycerol, glyceridacid and mixtures thereof.

11. The antiperspirant solution of claim 1 wherein the organic solvent is selected from the group consisting of ethylene glycol, polyethylene glycols, propylene glycol, dipropylene glycol, sorbitol, diethylene glycol, butylene glycol, hexylene glycol, 1,2-propylene glycol, 1,3 propylene glycol, glycerine, 1,2-hexanediol, hexanetriol, tripropylene glycol, propylene glycol methyl ether, isopropyl glycerol ether, dipropylene glycol methyl ether and combinations thereof at a concentration of about 1 to 10 weight percent.

12. The antiperspirant powder obtained by spray drying the solution of claim 1.

13. The antiperspirant powder obtained by spray drying the solution of claim 2.

14. The antiperspirant powder of claim 12 which have an average particle size of about 15 to 30 microns.

15. The antiperspirant powder of claim 12 which have bulk density from about 0.5 gm/cc to 2 gm/cc.

16. The antiperspirant powder of claim 12 which is micronized to have an average particle size of about 1 to 15 microns.

17. A method of preparing the antiperspirant solution comprising an (a) aluminum powder and (b) aluminum halide having the empirical formula $$Al_2(OH)_{6-x1}Y_{x1}Rp(AA)_q$$

wherein Y is Cl, Br, or .I and $1.3 \leq x_1 \leq 1.7$, wherein R is an organic solvent having at least two carbon atoms and at least one hydroxy group and p has a value of $0 \leq p \leq 1.0$ and wherein (AA) is amino acid or amino acid compound and $0 \leq q \leq 0.5$ and (i) size exclusion high performance liquid chromatography test band having a Band I relative area value of less than 5%, a Band II relative area value of 20% to 60%, Band III relative area value of 10% to 35% and Band IV relative area value of 15% to 50% and the sum of Band III and Band IV relative area value of at least 45% and no more than 70% and (ii) $^{27}$Al NMR spectrum wherein at least 45% of the total area under the spectrum from +100 ppm to -100 ppm is contained in the sum of the areas of resonance lines at or below 10 ppm and (iii) in which the area of the resonance at 63 ppm is less than 0.1% of the total area under the spectrum from +100 ppm to -100 ppm and which comprises the steps of reacting from about 30% to about 42% by weight of anhydrous basic aluminum halide antiperspirant active in water at a temperature greater than 85° C. but below the reflux temperature; maintaining this reaction until the reaction products attain an Al:halide ratio of 1.2:1 to 1.5:1 and solution solids concentration of about 30 to 42 weight percent on an anhydrous basis; cooling and filtering said reaction products; and aging reaction products at room temperature for a period of from about one day to 6 months until the desired size exclusion chromatograph is obtained.

18. The method of claim 17 in which the basic aluminum halide is obtained by taking a conventional basic aluminum halide solution having a suitable aluminum to halide ratio adjustable to an Al:halide ratio of the solution to about 1.2:1 to 1.5:1 and adding an appropriate amount of aged or unaged lower basicity aluminum halide solution or HX or $AlX_3 \cdot 6H_2O$ where X can be Cl, Br or I solution thereof and heating the aluminum halide solution to about 50–100° C. for a period that may range from about 10 minutes to about 6 hours and thereafter aging the resulting aluminum halide at room temperature until the desired chromatographic distribution of aluminum species is obtained.

19. The method of claim 17 wherein the said method comprises adding an organic solvent before, during or after aging.

20. The method claim 18 wherein the said method comprises adding an organic solvent before, during or after aging.

21. The method of claim 17 wherein the aged antiperspirant active is first buffered with amino acid and or salts of amino acids or mixtures thereof and further comprises addition of an organic solvent.

22. The method of claim 18 wherein the aged antiperspirant active is first buffered with amino acid and or salts of amino acids or mixtures thereof and further comprises addition of an organic solvent.

23. The method of claim 17 wherein the reaction product obtained is spray dried to powder.

24. The method of claim 18 wherein the reaction product obtained is spray dried to powder.

25. The method of claim 23 wherein the method further comprises micronizing or screening or air classification or combination thereof to achieve particles with a desired particle size distribution, particle shape distribution and density.

26. The method of claim 24 wherein the method further comprises micronizing or screening or air classification or combination thereof to achieve particles with a desired particle size distribution, particle shape distribution and density.

27. The method of claim 23 wherein in the spray drying uses an atomizer is selected from a csc disc, a two fluid nozzle, a single fluid nozzle, a multiple drilled hole disc or porous metal disc.

28. The method of claim 23 wherein the dried powder has a loss on drying when kept at 105° C. for 2 hrs. from about 5.0% to 20% by weight.

29. The method of claim 24 wherein the dried powder has a loss on drying when kept at 105° C. for 2 hrs. from about 5.0% to 20% by weight.

30. The method of making claim 25 wherein particles comprise thin walled or thick walled hollow spheres, solid spheres and irregular shaped non-hollow particles in different combinations to achieve the desired particle size and shape distribution.

31. The method of claim 26 wherein particles comprise thin walled or thick walled hollow spears, solid spheres and irregular shaped non-hollow particles in different combinations to achieve the desired particle size and shape distribution.

32. A method of making basic aluminum halides as in claim 23 wherein the critical humidity of the product is about 5–20%.

33. A method of making basic aluminum halides as in claim 24 wherein the critical humidity of the product is about 5–20%.

* * * * *

UNITED STATES PATENT AND TRADEMARK OFFICE
CERTIFICATE OF CORRECTION

PATENT NO. : 6,902,724 B1  
APPLICATION NO. : 10/807996  
DATED : June 7, 2005  
INVENTOR(S) : Parekh et al.

It is certified that error appears in the above-identified patent and that said Letters Patent is hereby corrected as shown below:

col. 1, line 47 - change "Band II" to --Band III-- col. 1, line 48 - change "In" to --IV-- col. 1, line 67 - change "Ala" to --Al $^a$-- col. 1, line 68 - change "Alb" to --Al $^b$-- col. 8, line 4 - change "DRAWING" to --DRAWINGS-- col. 8, line 24 - change "%" to --"-- col 11, line 42 -- change "ration" to --ratio-- col 14, line 50 - insert --are-- after "product"

col 16, line 7 - change "or 1" to --or I-- col 17, line 16 - change "or 1" to --or I-- col 18, line 46 - change "spears" to --spheres--

Signed and Sealed this

Twenty-sixth Day of September, 2006

JON W. DUDAS  
*Director of the United States Patent and Trademark Office*